US006592532B1

(12) United States Patent
Haung

(10) Patent No.: US 6,592,532 B1
(45) Date of Patent: Jul. 15, 2003

(54) MASSAGE ROD

(76) Inventor: Yeng-Shung Haung, No. 10, Sec. 2, Chung-Hsing Rd., Ho-Mei Chen, Changhwa Hsien (TW)

( * ) Notice: Subject to any disclaimer, the term of this patent is extended or adjusted under 35 U.S.C. 154(b) by 0 days.

(21) Appl. No.: 10/184,317

(22) Filed: Jun. 27, 2002

(51) Int. Cl.[7] ................................................ A61M 23/06
(52) U.S. Cl. ........................................ 601/107; 601/137
(58) Field of Search ........................... 601/80, 107, 111, 601/134–137; D24/211, 214

(56) References Cited

U.S. PATENT DOCUMENTS 904,650 A * 11/1908 Sampson ..................... 15/110
2,679,063 A * 5/1954 Hoffmann .................... 15/186
5,522,599 A * 6/1996 Kim ........................... 473/579
5,728,050 A * 3/1998 Lin ............................ 601/107
6,309,365 B1 * 10/2001 Lacey ........................ 601/137
6,450,980 B1 * 9/2002 Robbins et al. ............. 601/137

* cited by examiner

*Primary Examiner*—Justine R. Yu
(74) *Attorney, Agent, or Firm*—Alan D. Kamrath; Rider Bennett, LLP.

(57) ABSTRACT

A massage rod has a handle, a securing bushing and multiple massage twigs. The securing bushing is securely attached to one end of the handle. The massage twigs are securely connected to the handle with the securing bushing. Each massage twig has a straight section securely connected to the securing bushing and a spiral section integrally connected to the straight section. Accordingly, the contact area between the massage rod and the user's body is high and an excellent massage effect is provided.

6 Claims, 5 Drawing Sheets

MASSAGE ROD

BACKGROUND OF THE INVENTION

1. Field of the Invention

The present invention relates to a massage rod, and more particularly to a massage rod having multiple massage twigs with spiral sections to provide an excellent massage effect to the user.

2. Description of Related Art

Massage has been popular for thousands of years because of the need to relax aching muscles. With reference to FIG. 5, a conventional massage rod (30) in accordance with the prior art comprises a handle (32) and multiple massage twigs (34). The massage twigs (34) are made of metal and are securely attached to the handle (32), such that the free ends of the massage twigs will naturally flex and vibrate. When the user pats the body with the massage rod (30), the massage twigs (34),will massage the muscle and the acupuncture points so as to soothe the aches.

However, because each massage twig (34) of the conventional massage rod (30) is a straight twig, the conventional massage twig (34) cannot actually contact with the acupuncture points on the body and thus cannot provide a specific patting effect to the acupuncture points. In addition, the expansion area of the conventional straight massage twigs (34) is not enough to define a large contact area on the user's body, so the use of the conventional massage rod is not versatile. Furthermore, many massage twigs (34) are needed to form a large contact area, however the cost for manufacturing and the weight of the conventional massage rod (30) are too high.

To overcome the shortcomings, the present invention tends to provide a massage rod to mitigate or obviate the aforementioned problems.

SUMMARY OF THE INVENTION

The main objective of the invention is to provide a massage rod that has an excellent massage effect. The massage rod has a handle, a securing bushing and multiple massage twigs. The securing bushing is securely attached to one end of the handle. The massage twigs are securely connected to the handle with the securing bushing. Each massage twig has a straight section securely connected to the securing bushing and a spiral section integrally extending from the straight section. With such a massage rod, the contact area between the massage rod and the user's body is high. Multiple points that can actually contact and massage the acupuncture points on the body are formed on each respective massage twig. An excellent massage effect is provided.

Other objects, advantages and novel features of the invention will become more apparent from the following detailed description when taken in conjunction with the accompanying drawings.

DETAILED DESCRIPTION OF PREFERRED EMBODIMENT

Figure 1:
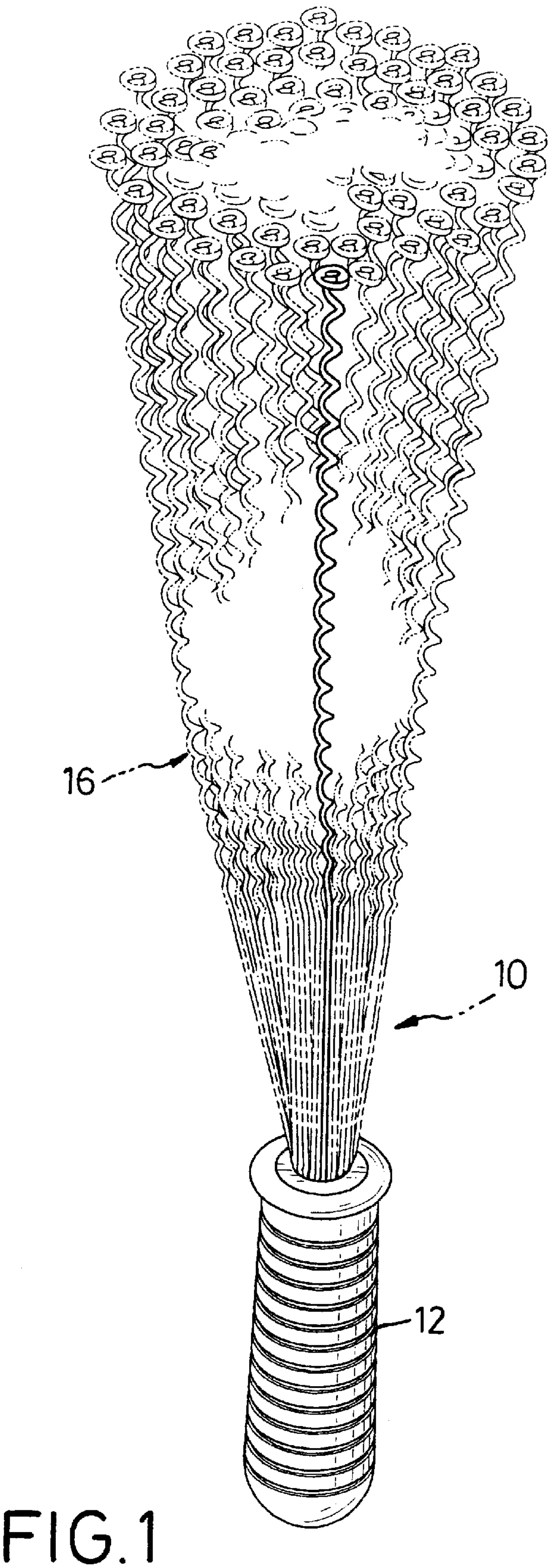
FIG. 1 is a perspective view of a massage rod in accordance with the present invention.
Figure 2:
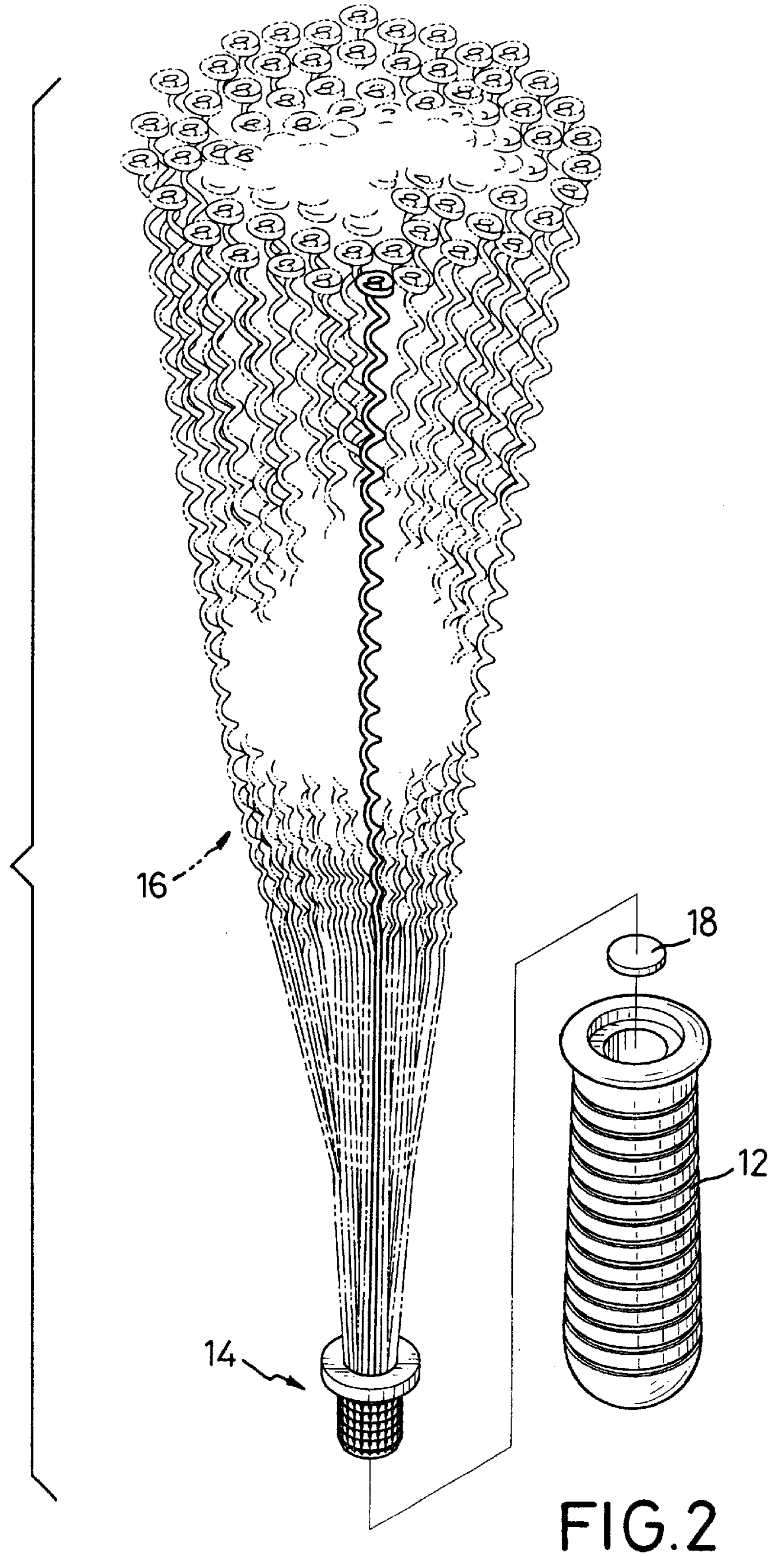
FIG. 2 is an exploded perspective view of the massage rod in FIG. 1.
Figure 3:
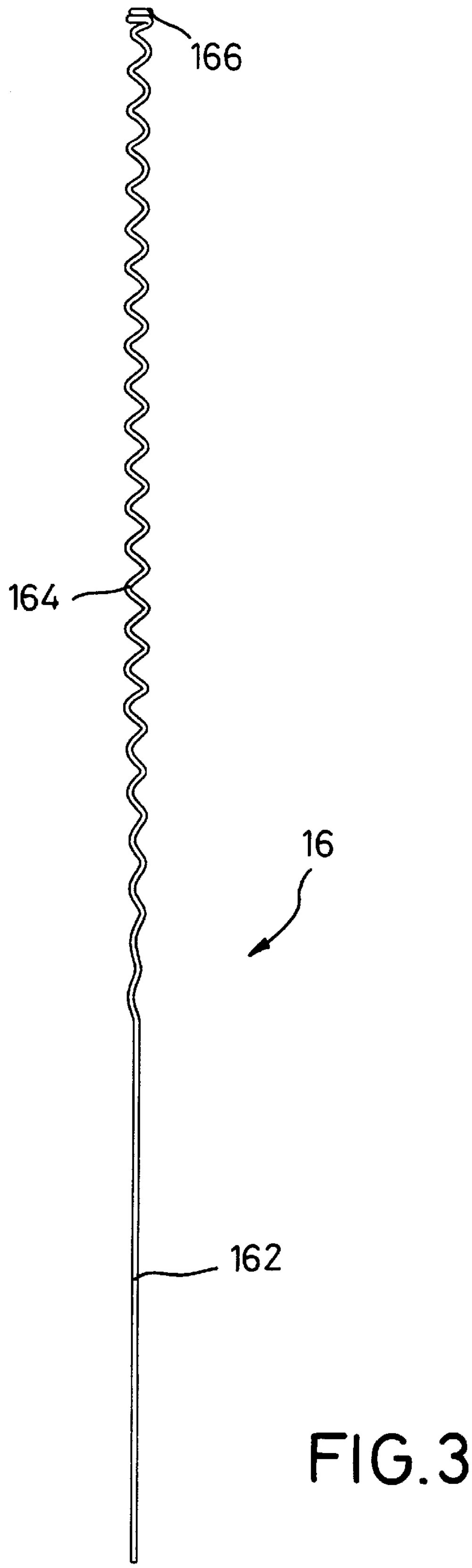
FIG. 3 is a perspective view of a massage twig of the massage rod in FIG. 1.
Figure 4:
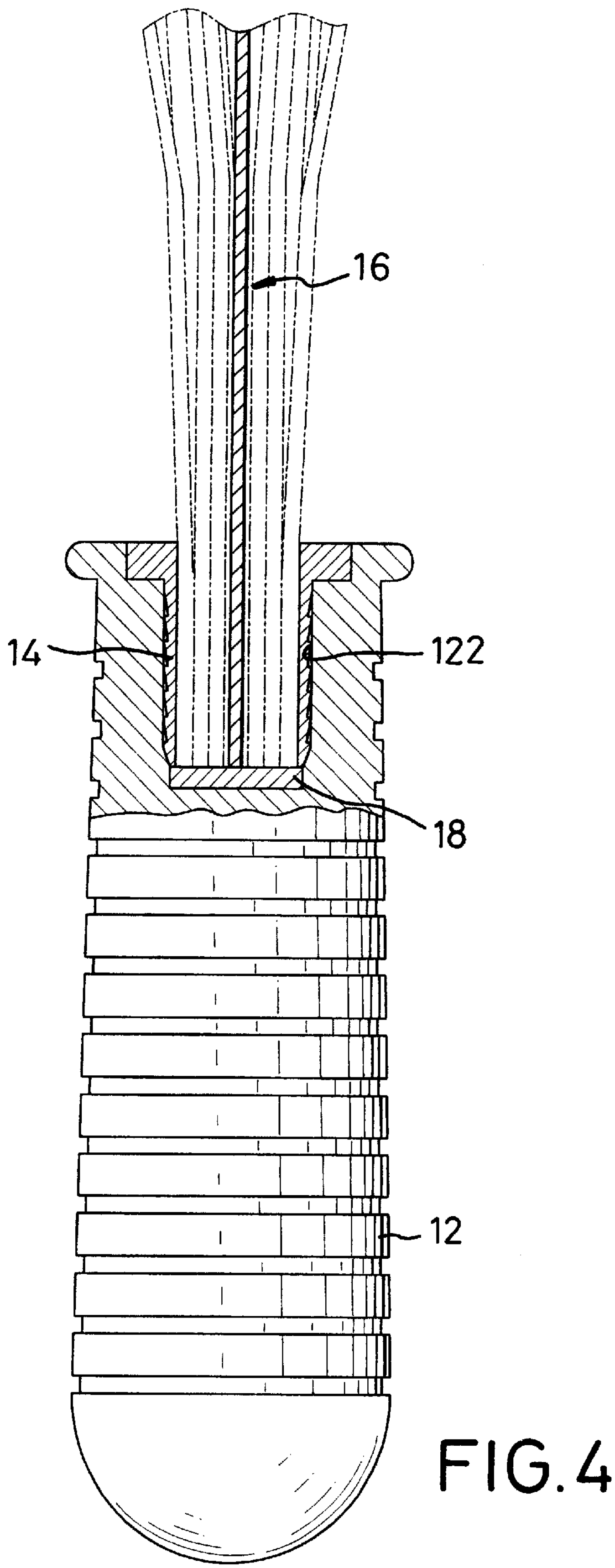
FIG. 4 is a side plan view in partial cross section of the massage rod in FIG. 1.

With reference to FIGS. 1 to 4, a massage rod (10) in accordance with the present invention comprises a handle (12), a securing bushing (14) and multiple massage twigs (16). A hole (not numbered) is defined in the handle (12) for securely receiving the securing bushing (14). The securing bushing (14) is securely received in the hole in the handle (12) and has a central hole (not numbered) defined through the securing bushing (14). In practice, the securing bushing (14) has an outer diameter smaller than an inner diameter of the hole in the handle (12) so that the securing bushing (14) is securely pressed into the hole in the handle (12). A rough outer surface is formed on the securing bushing (14), such that the friction between the securing bushing (14) and the inner surface of the hole in the handle (12) is increased. This can enhance the combination between the handle (12) and the bushing (14).

The massage twigs (16) are securely attached to the securing bushing (14). Each massage twig (16) has a straight section (162) formed on one end of the massage twig (16) and having one end securely accommodated in the central hole in the securing bushing (14). A spiral section (164) integrally extending from the straight section (162) is formed on each respective massage twig (16) and is far from the securing busing (14). A coil end (166) is formed on the free end of each respective massage twig (16) and is integrally connected to the spiral section (164) of the massage twig (16). With the arrangement of the coil end (166), sharp free ends of the massage twigs (16) will not hurt the user. In addition, a magnet (18) is received in the hole of the handle (12) and abuts the massage twigs (16).

Figure 5:
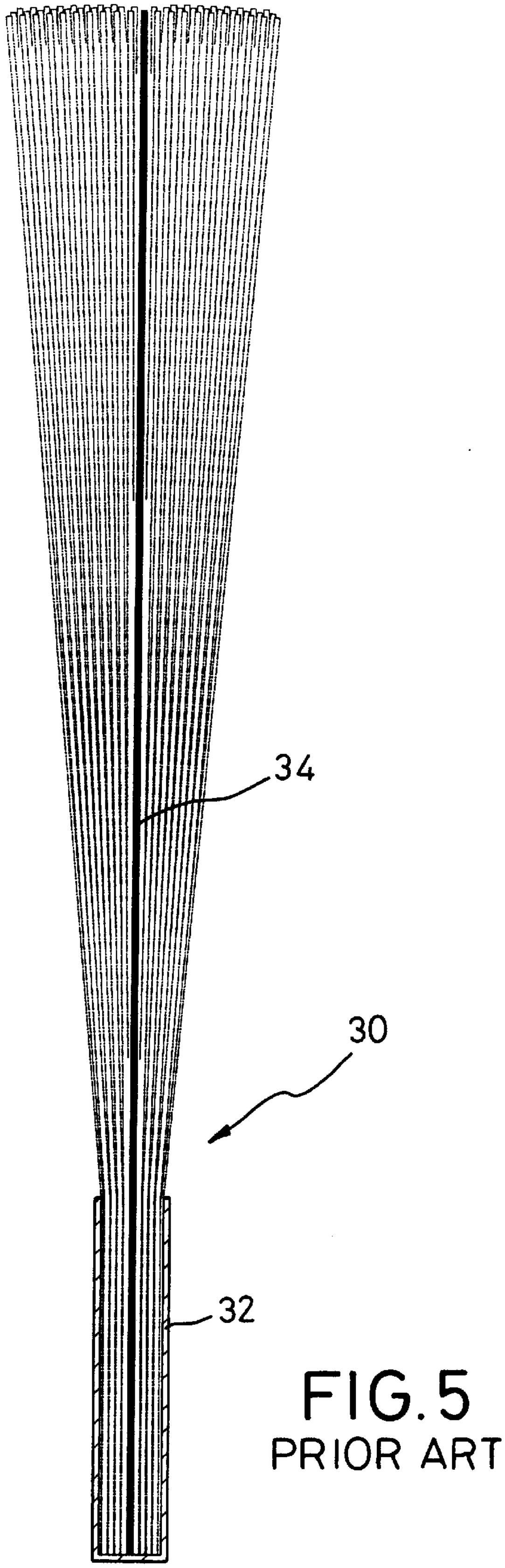
FIG. 5 PRIOR ART
FIG. 5 is a side plan view in partial cross section of a conventional massage rod in accordance with the prior art.

In such an arrangement, because there is a spiral section (164) formed on each massage twig (16), multiple massage points will be formed on each respective massage twig (16) at the bent locations of the spiral section (164). When the massage twigs (16) are patted on the body of the user, the massage twigs (16) can provide excellent massage effects to the user's body by means of the massage points actually contacting the acupuncture points. The massage effect of the massage rod (10) is better than that of the conventional massage rod (30) with straight massage twigs (34) as shown in FIG. 5. In addition, the expansion area of the free ends of the massage twigs (16) will be large due to the arrangements of the spiral sections (164), such that the contact area between the massage rod (10) and the user's body is high. The amount of the massage twigs (16) required for a large coverage is small, and the cost for manufacturing and weight of the massage rod (10) are both low. In addition, with the arrangement of the magnet (18), a magnetic massage effect can be achieved so that the use of the massage rod (10) is versatile.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A massage rod comprising:

a handle;

a securing bushing securely attached to one end of the handle; and multiple massage twigs securely connected to the handle with the securing bushing, each having a straight section securely connected to the securing bushing and a spiral section integrally connected to the straight section and far from the securing bushing.

2. The massage rod as claimed in claim 1, wherein the securing bushing has a central hole defined through the securing bushing for the straight sections of the massage twigs being securely accommodated in the central hole.

3. The massage rod as claimed in claim 2, wherein the handle has a hole defined in the handle for securely receiving the securing bushing; and the securing bushing has an outer diameter smaller than an inner diameter of the hole in the handle so that the securing bushing is securely pressed into.the hole in the handle.

4. The massage rod as claimed in claim 3, wherein the securing bushing has a rough outer surface to increase friction between the securing bushing and an inner surface of the hole in the handle.

5. The massage rod as claimed in claim 2 further comprising a magnet received in the hole of the handle and abutting the massage twigs.

6. The massage rod as claimed in claim 1 further comprising a coil end formed on a free end of each respective massage twig and integrally connected to the spiral section of the massage twig.

* * * * *